US004001670B2

United States Statutory Invention Registration [19]

[11] Reg. Number: H1670

[45] Published: Jul. 1, 1997

Aziz et al.

[54] ABSORBENT ARTICLE HAVING A NONWOVEN AND APERTURED FILM COVERSHEET

[76] Inventors: Mohammed Iqbal Aziz, Jl. Kemang Timur IV No. 10, Kelurahan Bangka I, Jakarta Seltan, Indonesia; Sharon Darlene Kirkpatrick, 6100 Center Hill Rd., Cincinnati, Ohio 45224; Robert William Ruuska, 6100 Center Hill Rd., Cincinnati, Ohio 45224; Robert Eugene Askin, II, 6100 Center Hill Rd., Cincinnati, Ohio 45224

[21] Appl. No.: 492,352

[22] Filed: Jun. 19, 1995

Related U.S. Application Data

[60] Continuation of Ser. No. 322,910, Oct. 13, 1994, abandoned, which is a division of Ser. No. 72,660, Jun. 4, 1993, abandoned, which is a continuation of Ser. No. 794,745, Nov. 9, 1991, abandoned.

[51] Int. Cl.[6] ..... A61F 13/15

[52] U.S. Cl. ..... 604/367

[58] Field of Search ..... 604/358, 365–366, 604/370, 373, 377, 378–384

[56] References Cited

U.S. PATENT DOCUMENTS 3,945,386 3/1976 Anczurowski et al. .
3,967,623 7/1976 Butterworth et al. .
4,077,410 3/1978 Butterworth et al. .

*Primary Examiner*—Charles T. Jordan
*Assistant Examiner*—Meena Chelliah

[57] ABSTRACT

An absorbent article having improved strikethrough, rewet characteristics, and feel is disclosed. The absorbent article has a topsheet comprising a nonwoven material and apertured thermoplastic film. The apertured thermoplastic film is treated with a surfactant preferably by incorporating the surfactant into the resin used to make the thermoplastic film. The combination of the nonwoven material and the surfactant-treated apertured thermoplastic film permit liquids to rapidly penetrate the topsheet while preventing liquid in the absorbent core of the article from flowing back through the topsheet. The nonwoven material provides the topsheet with improved, less plastic-like feel.

7 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLE HAVING A NONWOVEN AND APERTURED FILM COVERSHEET

This is a continuation of application Ser. No. 08/322,910, filed on Oct. 13, 1994, which is a division of application Ser. No. 08/072,660, filed on Jun. 4, 1993, which is a continuation of application Ser. No. 07/794,745, filed on Nov. 9, 1991 all now abandoned.

FIELD OF THE INVENTION

This invention relates to absorbent articles such as diapers, incontinent articles, sanitary napkins, and the like. More particularly, this invention relates to absorbent articles having a nonwoven and apertured film coversheet.

BACKGROUND OF THE INVENTION

All manner and variety of absorbent articles configured for the absorption of body fluids are, of course, well known. Current types of absorbent articles include diapers, incontinent articles, and sanitary napkins.

A major in use problem encountered with known absorbent articles is leakage of waste product which contaminates clothing articles that contact the absorbent article, such as pants, shirts, and bedding. The amount of leakage experienced by the wearer can be reduced by improving the rate at which the liquid enters the absorbent core. Thus, an absorbent article in which the liquid rapidly penetrates the topsheet and is contained in the absorbent core will experience less leakage than an absorbent article in which liquid is able to run across the topsheet before penetrating into the absorbent core. Reducing run-off, therefore, reduces the amount of leakage experienced with the absorbent article.

Another in-use problem associated with absorbent articles is the dryness of the skin contacting surface. Generally, the drier the skin contacting surface, the more comfortable the absorbent article. There have been several patents directed towards reducing the surface wetness in disposable diaper structures. U.S. Pat. No. 3,945,386 issued to Anczurowski on Mar. 23, 1976 and U.S. Pat. Nos. 3,965,906 and 3,994,299 issued to Karami on Jun. 29, 1976 and Nov. 30, 1976, respectively, teach diaper structures having a perforated thermoplastic film interposed between the topsheet and the absorbent core. U.S. Pat. No. 4,324,247 issued to Aziz on Apr. 13, 1982 describes an effort directed to both reducing run-off and reducing the surface wetness of absorbent articles.

Still another problem associated with absorbent articles is the feel of the skin contacting surface. A problem with utilizing formed films is that some consumers do not like the plastic feel associated with such films. A number of efforts have been directed at improving the feel of the surface of absorbent articles. One effort is described in U.S. Pat. No. 3,967,623 issued to Butterworth, et al. The Butterworth patent is directed to an absorbent pad having a facing sheet comprising a perforated thermoplastic web having an integral fibrous or sueded outer surface.

The products described in most of the above references, however, are less than ideal in achieving a good combination of all three desired properties of reduced surface run-off, improved rewet characteristics, and improved feel. While the product described in the Aziz patent works quite well, the search for improved coversheets has continued.

It is therefore an object of the present invention to provide an absorbent article having a good combination of reduced surface run-off characteristics, improved surface dryness, and an improved softer, less plastic-like feel.

Other objects of the present invention will become more fully apparent in the following description of the embodiments of this invention and from the appended claims.

SUMMARY OF THE INVENTION

This invention relates to absorbent articles such as diapers, incontinent articles, sanitary napkins, and the like. More particularly, this invention relates to absorbent articles having a nonwoven and apertured film coversheet.

The absorbent article comprises, in its basic form, a liquid pervious coversheet (or topsheet), a liquid impervious backsheet joined to the topsheet, and an absorbent core positioned between the topsheet and backsheet. The topsheet is comprised of a nonwoven material, preferably a nonwoven fabric, and an apertured plastic film. The apertured plastic film preferably has a multiplicity of tapered capillaries. The capillaries enable the film to transport liquid through the topsheet to the absorbent core and prevent liquid from flowing in the reverse direction. At least the film, and preferably both the nonwoven fabric and the film, are treated with a surfactant to enhance the permeability completely through the topsheet.

The resulting absorbent article is believed to exhibit a good combination of all three desired characteristics of reduced surface run-off and improved surface dryness characteristics, as well as improved feel.

DESCRIPTION OF THE PREFERRED EMBODIMENTS

Figure 1:
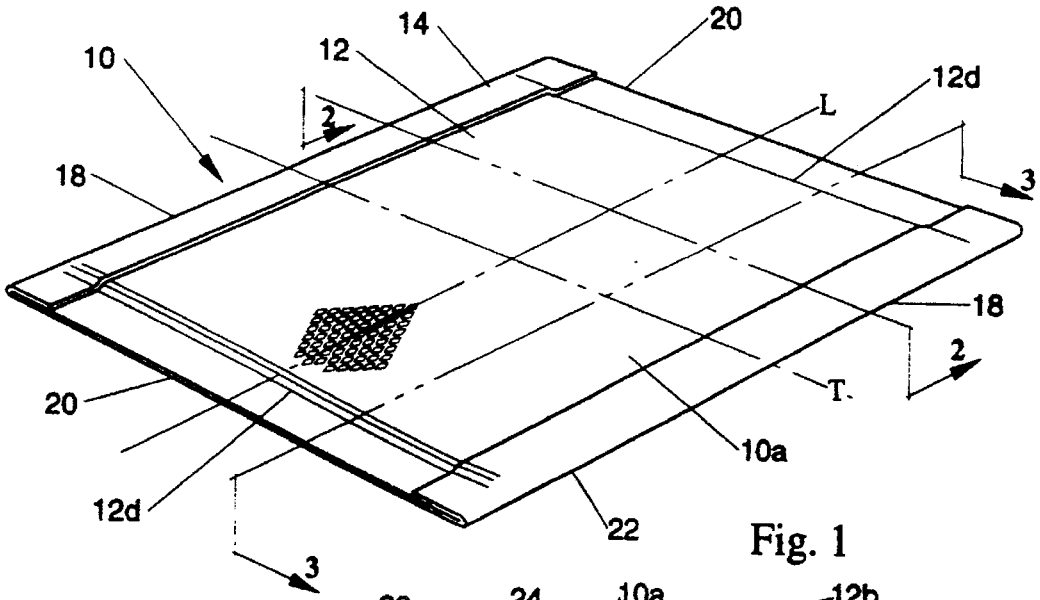
FIG. 1 is a simplified perspective view of an absorbent article of the present invention.

1. The Absorbent Article.

This invention relates to absorbent articles such as diapers, incontinent articles, sanitary napkins, and the like. More particularly, this invention relates to absorbent articles having a nonwoven and apertured film coversheet.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include diapers, incontinent articles, sanitary napkins, pantiliners, and other articles used to absorb body exudates. The term "disposable" refers to articles which are intended to be discarded after a single use and preferably recycled, composted, or otherwise disposed of in an environmentally compatible manner. (That is, they are not intended to be laundered or otherwise restored or reused as an absorbent article.)

The term "diaper" refers to a garment generally worn by infants and incontinent persons which is drawn up between the legs and fastened about the waist of the wearer. Suitable diapers that can be provided with the coversheet described herein are disclosed in U.S. Pat. Re. No. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986; U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany, et al. on May 30, 1989; U.S. Pat. No. 4,888,231 issued to Angstadt on Dec. 19, 1989; and U.S. Pat. No. 4,909,803 issued to Aziz, et al. on Mar. 20, 1990.

The term "incontinent article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the coversheet described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. Nos. 4,704,115; 4,909,802 issued to Ahr, et al.; U.S. Pat. No. 4,964,860 issued to Gipson, et al. on Oct. 23, 1990; and in U.S. Pat. Application Ser. Nos. 07/637,090 and 07/637,571 filed respectively by Noel, et al. and Feist, et al. on Jan. 3, 1991.

The term "sanitary napkin" refers to an article which is worn by females adjacent to the pudendal region that is intended to absorb and contain various exudates which are discharged from the body (e.g., blood, menses, and urine). Suitable sanitary napkins that can be provided with the coversheet described herein are disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264 , and 5,009,653 issued to Osborn on Aug. 21, 1990 and Apr. 23, 1991, respectively; and in U.S. Pat. Application Ser. No. 07/605,583 filed Oct. 29, 1990 in the name of Visscher, et al.

The term "pantiliner" refers to absorbent articles that are less bulky than sanitary napkins which are generally worn by women between their menstrual periods. Suitable pantiliners that can be provided with the coversheet described herein are disclosed in U.S. Pat. No. 4,738,676 entitled "Pantiliner" issued to Osborn on Apr. 19, 1988.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

Figure 2:
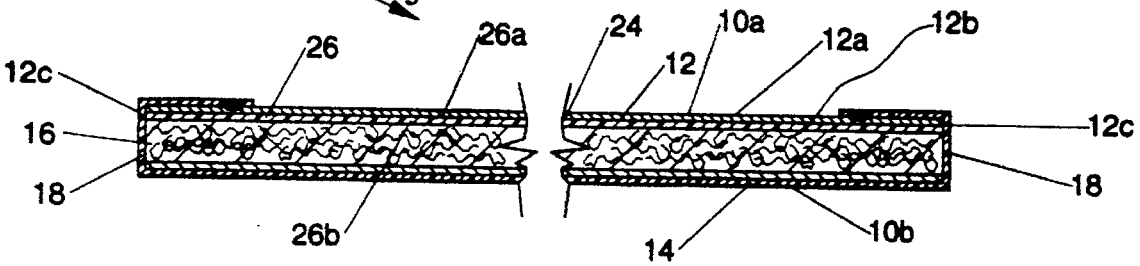
FIG. 2 is a cross-sectional view taken along line 2—2 of FIG. 1.
Figure 3:
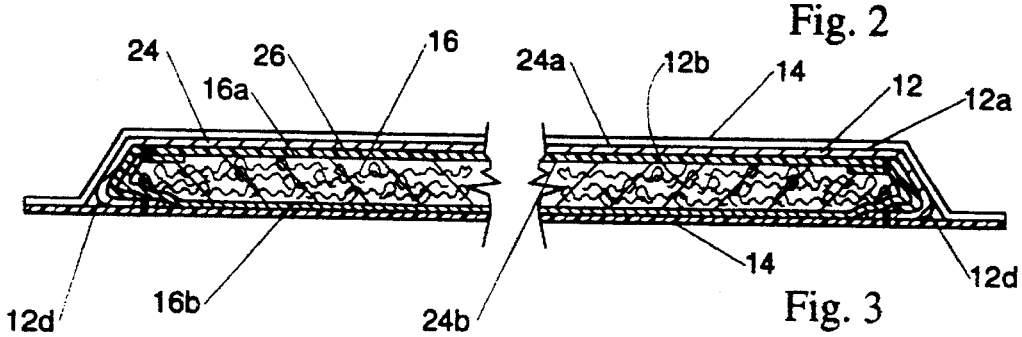
FIG. 3 is a cross-sectional view taken along line 3—3 of FIG. 1.

FIG. 1 shows a simplified absorbent article 10 that could represent a diaper prior to its being placed on a wearer. It should be understood, however, that the present invention is not limited to the particular type or configuration of absorbent article shown in the drawings. As shown in FIG. 2, such an absorbent article 10 basically comprises topsheet 12, backsheet 14, and absorbent core 16.

The absorbent article 10 has two surfaces, a body-contacting surface (or "body surface") 10*a* and a garment surface lob. The body surface 10*a* is intended to be worn adjacent to the body of the wearer. The garment surface lob of the absorbent article 10 (shown in FIG. 2) is on the opposite side and is intended to be placed adjacent to the wearer's undergarments or clothing when the absorbent article 10 is worn.

The absorbent article 10 has two centerlines, a longitudinal centerline 1 and a transverse centerline t. The terms "longitudinal" and "transverse" or "lateral" (the latter two being interchangeable), are defined in U.S. Pat. No. 5,007,906 issued to Osborn, III, et al. and are applicable to the absorbent articles described herein. FIG. 1 shows that the absorbent article 10 has two spaced apart longitudinal edges 18 and two spaced apart transverse or end edges (or "ends") 20, which together form the periphery 22 of the absorbent article 10.

The individual components of the absorbent article 10 will now be looked at in greater detail.

The topsheet 12 is compliant, soft-feeling and non-irritating to the wearer's skin. Further, topsheet 12 is liquid permeable, permitting liquids to readily penetrate through its thickness. The topsheet 12 has a body-facing side or face 12*a* and a garment-facing side or face 12*b*, two longitudinal or side edges 12*c* and two end edges 12*d*. (A similar numbering system will be used for the other components of the diaper 10. That is, the side of the component facing the wearer's body will be designated by the number of the component and a reference letter "a", the side facing the wearer's undergarments by the number of the component and the letter "b", and the side and end edges by the number of the component and the reference letters "c" and "d" respectively.)

The topsheet 12 comprises two components, a nonwoven material, preferably in the form of a fabric 24, and a three dimensional apertured plastic film 26. The garment-facing side or face 24*b* of the nonwoven fabric 24 is preferably maintained in close contact with, and more preferably bonded to, the body-facing face 26*a* of the apertured plastic film 26. The component parts of the topsheet 12 are examined in greater detail below.

The nonwoven fabric 24 may be any nonwoven fabric that is permeable to liquids. A suitable nonwoven fabric 24 may be manufactured from a wide range of materials such as natural fibers (e.g., wood or cotton fibers), synthetic fibers (e.g., polyester, polypropylene) or a combination thereof. The nonwoven fabric 24 is preferably made from fibers selected from a group consisting of polypropylene, polyester, polyethylene, polyvinylalcohol, starch base resins, polyurethanes, cellulose and cellulose esters.

Clearly, there are a number of manufacturing techniques which may be utilized to manufacture the nonwoven fabric 24. For example, nonwoven fabric 24 may be resin-bonded, needle punched, spunbonded, carded, the latter including, thermally bonded, air-thru bonded, and spunlaced fabrics. A preferred nonwoven fabric 24 is a thermally bonded polypropylene fabric.

Figure 4:
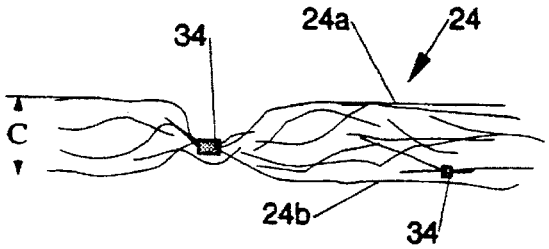
FIG. 4 is an edge view of the nonwoven fabric comprising part of the topsheet of the absorbent article.

The nonwoven fabric 24 should be lightweight having a weight from about 1 to about 40 g/sq m, preferably from about 1 to about 23 g/sq.m. For one embodiment, the nonwoven fabric 24 has a basis weight range of from about 18 to about 22 grams per square yard (about 21 to about 26 g/sq.m.) and a caliper C as shown in FIG. 4, of from about 5 to about 15 mils (about 0.13 to about 0.38 mm.) when measured under a load of about 200 pascals. Such a nonwoven fabric 24 is further characterized by a minimum wet or dry tensile strength of at least about 400 grams per centimeter in the longitudinal or machine direction and at least about 55 grams per centimeter in the cross machine direction.

In another embodiment, the nonwoven fabric 24 has a lighter weight of from about 8 to about 12 g/sq m. Such lighter nonwoven fabrics are highly preferred. They are preferred because they can be used (with a lightweight film) to form a composite topsheet 12 that is sufficiently thin and lightweight that it behaves as a single sheet of material. This provides the advantages that such a topsheet may be more flexible and use smaller amounts of raw materials.

The nonwoven fabric 24 preferably has a pattern of thermal bond sites 34. One preferred nonwoven fabric comprises a carded thermally dot bonded polypropylene web. The thermal bonds in such a fabric are preferably rectangularly-shaped in plan view. The bonds are preferably arranged in staggered rows. Another preferred nonwoven is a spunbonded polypropylene web with similarly arranged thermal bonds. Still another preferred nonwoven fabric 24 is a carded polypropylene web which is embossed in accordance with the method described in U.S. Pat. No. 4,781,710 issued to Megison, et al. This nonwoven fabric 24 has embossed and thermal bonded areas that are diamond-shaped in plan view. The diamond-shaped bonds are spaced apart and arranged in a diamond-shaped grid such as is shown in FIGS. 1 and 2 of the Megison, et al. patent. (The embossing need not extend into the underlying core, however.)

Figure 5:
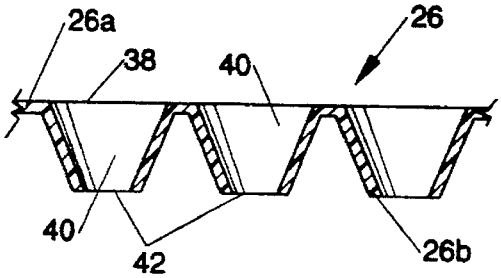
FIG. 5 is an edge view of the apertured plastic film comprising the other component of the topsheet.

The apertured plastic film 26 is preferably located between the nonwoven fabric 24 and the absorbent core 16. As shown in FIG. 5, the apertured plastic film 26 is preferably a three-dimensional structure which has a plurality of tapered capillaries 40, each of which has a base opening 38, and an apex opening 42. The apex openings 42 are preferably in intimate contact with the absorbent core 16.

The apertured plastic film 26 is manufactured from a liquid impervious, preferably thermoplastic material. One suitable material is a low density polyethylene film having a thickness of from 0.001 to 0.002 inches (0.0025 to 0.0051 cm.). The thermoplastic material for use in the manufacture of the apertured plastic film 26 is selected from a group consisting generally of polyethylene, polypropylene, polyvinyl chloride, starch base resins, polyvinylalcohol, polyurethanes, polycaprolactone and cellulose esters. The thermoplastic material used in the present invention preferably has a density in the range of from about 0.90 g/cm$^3$ to about 1.20 g/cm$^3$, with the more preferred range of densities being from about 0.91 g/cm$^3$ to about 0.92 g/cm$^3$. The general melt indices range for such material is preferably from about 2 to about 100, with the more preferred range being from about 4 to about 25.

In one preferred embodiment, the thermoplastic material is provided with a multiplicity of tapered capillaries 40 in a manner, size, configuration, and orientation set forth in U.S. Pat. No. 3,939,135 issued to Thompson on Dec. 30, 1975. Other suitable apertured plastic films are disclosed in U.S. Pat. No. 4,324,426, issued to Mullane, et al. on Apr. 13, 1982, U.S. Pat. No. 4,342,314, issued to Radel, et al. on Aug. 3, 1982, and U.S. Pat. No. 4,463,045, issued to Ahr, et al. on Jul. 31, 1984. The apertured plastic film 26 can comprise other types of apertured plastic films that are not thermoplastic. The type of film used depends on the type of processing the film and nonwoven components are subjected to during the manufacture of the topsheet 12. Thermoplastic films are used when the nonwoven fabric 24 and the film 26 are integrally formed into a composite structure by melting. Other suitable types of apertured films include, but are not limited to hydro-formed films. Hydro-formed films are described in at least some of the following U.S. Pat. Nos.: 4,609,518, 4,629,643, 4,695,422, 4,772,444, 4,778,644, and 4,839,216 issued to Curro, et al., and U.S. Pat. No. 4,637,819 issued to Ouellette, et al.

The nonwoven fabric 24 and the apertured plastic film 26 may be placed into a face-to-face relationship. The two components may be secured or unsecured. The two components, if secured, may be secured to each other by many different methods (or securement means) or combinations of methods. Suitable methods for securing the two components include, but are not limited to adhesives, fusion including heat bonding and/or pressure bonding, ultrasonics, and dynamic mechanical bonding.

The adhesives can be applied in a uniform continuous layer, a patterned layer, or an array of separate lines, spirals, beads, or spots of adhesive. The adhesive attachment preferably comprises an open pattern network of filaments of adhesive as is disclosed in U.S. Pat. No. 4,573,986 issued to Minetola, et al. on Mar. 4, 1986, or an open pattern network of filaments comprising several lines of adhesive filaments swirled into a spiral pattern as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. A method of heat/pressure bonding that could be used is described in U.S. Pat. No. 4,854,984 issued to Ball, et al. on Aug. 8, 1989.

The nonwoven, fabric 24 and the apertured plastic film 26 may alternatively be indirectly secured. For instance, the two components could be secured to or through a thin layer of airfelt, or a layer-of hydrophobic material positioned between the nonwoven fabric 24 and the apertured plastic film 26. Preferably, such additional layer or layers are treated with a surfactant (as described in greater detail below).

The nonwoven fabric 24 and the apertured plastic film 26 can alternatively be integrally formed into a composite structure. The terms "composite" "composite structure" or "combination", as used herein, refer to relationships in which portions of the nonwoven fabric 24 extend into the film 26, and vice versa so that they are integrally attached. These components cease to exist as separate layers in a face-to-face relationship.

Figure 6:
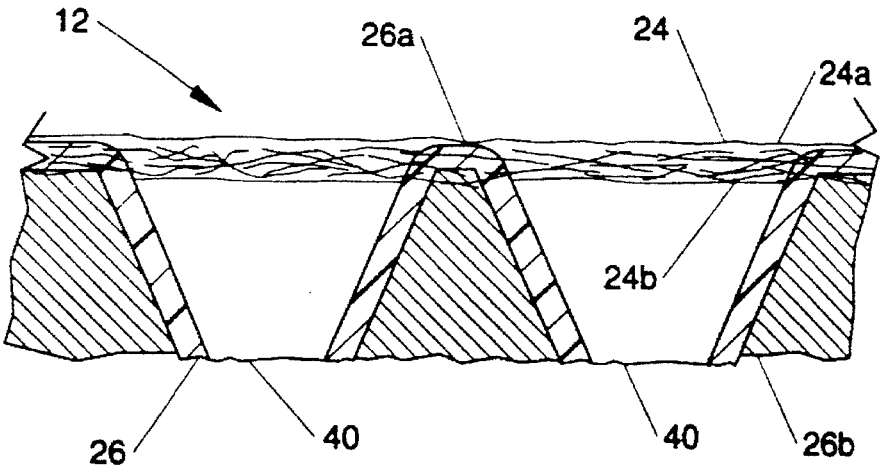
FIGS. 6–8 are edge views of alternative embodiments of the completely assembled topsheet.
Figure 7:
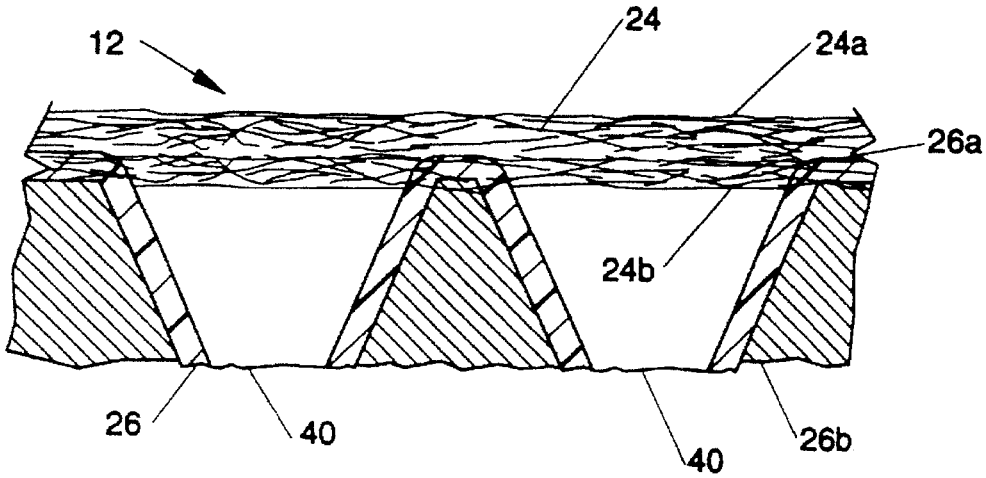
Figure 8:
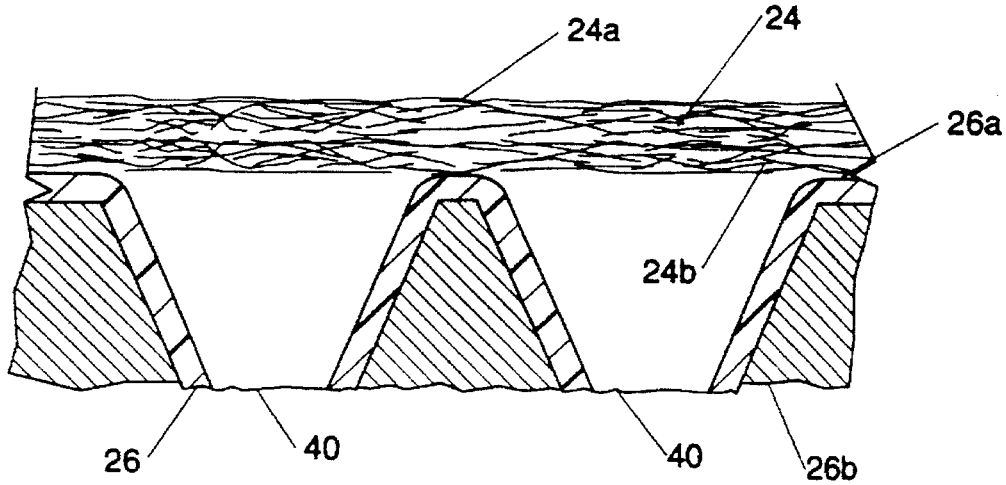

FIGS. 6 and 7 show several possible embodiments of such a composite structure. In the embodiments shown, at least a portion of the fibers in the nonwoven web 24 are embedded in some portion of the thermoplastic film 26. The relationship between the surfaces of the respective components differs in each embodiment. However, in both embodiments shown in FIGS. 6 and 7, the garment-facing face **24*b* of the nonwoven material 24 is positioned between the body-facing and garment-facing surfaces of the apertured film 26. These can be contrasted with the embodiment shown in FIG. 8** in which the components are separate layers in a face-to-face relationship.

FIG. 6 shows an example of a composite structure in which the body-facing sides of the two components, **24*a* and 26*a*, lie in approximately the same plane. FIG. 7 shows a composite structure in which the body-facing side 24*a* of the nonwoven material 24 is above that of the film 26 so the body-facing side 26*a* of the film 26 is positioned between the surfaces of the nonwoven fabric 24. The embodiment shown in FIG. 7 is believed to be the more preferable of these two embodiments because it provides the softer nonwoven fabric 24 over the entire body-facing surface 12***a* of the topsheet 12. This can be contrasted with the embodiment shown in FIG. 6. In the embodiment shown in FIG. 6, portions of the fibers comprising the nonwoven fabric 24 are embedded into the film along at least a portion of the body-facing surface 12a of the topsheet 12. These embedded portions are typically not as soft as the nonwoven material alone.

In other alternative embodiments, the topsheet 12 could be constructed so that the film 26 underlies only a portion of the area of the nonwoven fabric 24. For example, the film 26 may be of a smaller size that it only covers the portion of the absorbent article into which liquids are deposited or absorbed. This could be in the crotch region of the absorbent article or in a urine "target zone".

The absorbent core 16 is positioned between the topsheet 12 and the backsheet 14. The absorbent core 16 provides the means for absorbing bodily exudates. The absorbent core 16 need not have an absorbent capacity much greater than the total amount of exudates to be absorbed. The absorbent core 16 is generally compressible, conformable, and non-irritating to the user's skin. It can comprise any material used in the art for such purpose. Examples include comminuted wood pulp which is generally referred to as airfelt, creped cellulose wadding, cross-linked cellulose fibers, absorbent foams, absorbent sponges, synthetic staple fibers, polymeric fibers, hydrogel-forming polymer gelling agents, peat moss, combinations of the foregoing, or any equivalent material or combinations of materials.

Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,889,596, issued Dec. 26, 1989 to Schoggen, et al.; U.S. Pat. No. 4,898,642, issued Feb. 6, 1990 to Moore, et al.; and U.S. Pat. No. 4,935,022, issued Jun. 19, 1990 to Lash, et al.

The characteristics of the absorbent core 16 for particular types of absorbent articles are described in greater detail in the patents and documents incorporated by reference herein, and the patents and other documents incorporated by reference in those documents, the disclosures of which are all incorporated by reference herein. Other suitable absorbent core arrangements are described in U.S. Pat. Nos. 4,988,344 and 4,988,345, and European Patent Application Publication No. 0 198 683, published Oct. 22, 1986 in the name of Duenk, et al. which are also incorporated by reference herein. The absorbent article 10 could also include any additional layers or other components such as are described in the patents incorporated by reference. For example, the absorbent article 10 may comprise an acquisition layer or patch of cross-linked cellulose fibers positioned between the topsheet 12 and the absorbent core 16.

The backsheet 14 is impervious to liquids and is preferably manufactured from a thin plastic film, although other flexible liquid impervious materials may also be used. The backsheet 14 prevents liquid contained in absorbent core 16 from wetting articles which contact the absorbent article 10. Polyethylene films having a thickness of from about 0.001 to about 0.002 inches (0.0025 to 0.0051 cm.) have been used for the backsheet 14 with satisfactory results. As used herein, the term "flexible" refers to materials which are compliant and which will readily conform to the general shape and contours of the human body.

The backsheet 14 is superimposed on the garment-facing side 16*b* of absorbent core 16 and preferably extends beyond the edges thereof. The topsheet 12 is superimposed over the body-facing side 16*a* of the absorbent core 16, and may also extend beyond the edges of the core 16. The absorbent core 16 is, therefore, positioned between the topsheet 12 and the backsheet 14. The topsheet 12 and backsheet 14 are joined to each other such as around their peripheries. The topsheet 12 and backsheet 14 can be joined in any suitable manner such as by the use of adhesives, crimping, heat-sealing, or ultrasonic bonding. A more detailed description of how topsheet 12, backsheet 14, and absorbent core 16 may be assembled for particular types of absorbent articles is provided in the documents incorporated by reference herein.

2. Method of Making the Absorbent Article.

Figure 9:
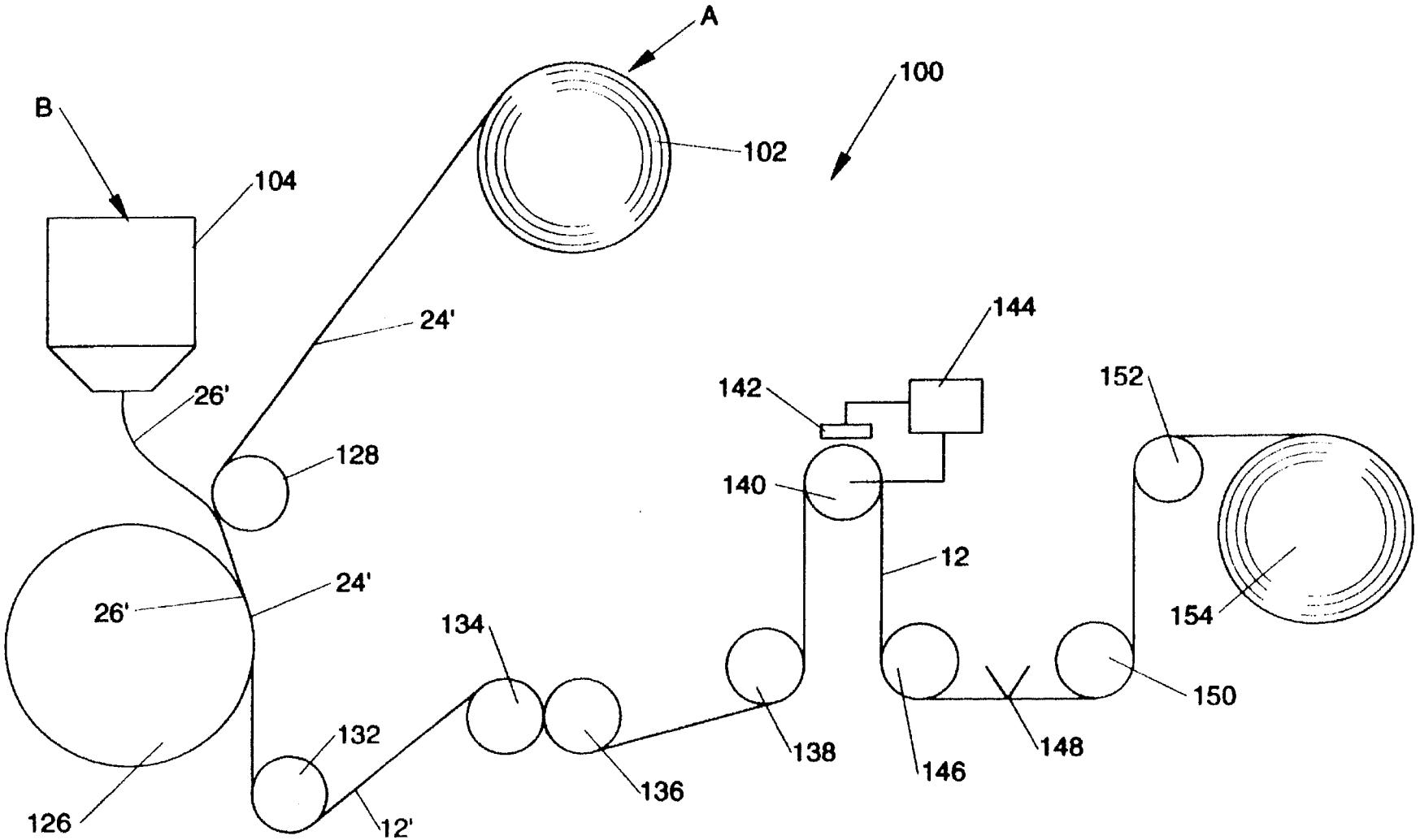
FIG. 9 is a schematic representation of one process for making a coversheet for the absorbent article.

A suitable process of preparing the topsheet 12 is shown in FIG. 9. One version of the process described below is also set forth in U.S. Pat. Application Ser. No. (Serial No. not yet assigned) filed in the name of Lowe by Tredegar Film Products on the same day as the present application.

The apparatus for making the topsheet for the absorbent article of the present invention is designated 100. The apparatus 100 includes a first supply source 102 and a second supply source 104. The supply sources (or "supply means") 102 and 104 feed the materials that will comprise the components of the topsheet into the system.

The nonwoven material is fed into the process at the place indicated by the letter A. The first supply source 102 feeds a first material 24' used to make the nonwoven fabric 24 into the system. The first material 24' can be any of those materials specified above as being suitable for use in or as the nonwoven fabric 24. The nonwoven material may be supplied by any suitable supply source. The first supply source 102 could include, but is not limited to any conventional means used to introduce a material into a laminating process. The first supply source 102 could be, but is not limited to an unwind roll; a web or fabric producing machine, such as a conventional carding machine, spunbonding machine; or a hopper for feeding a layer of loose fibers into the system.

In the process illustrated, the first supply source comprises a supply roll 102 which holds first material in the form of a nonwoven fabric web 24'. The nonwoven fabric web 24' is preferably of a thin, soft construction. Some preferred nonwoven fabrics are manufactured by the Fiberweb Group under the trademarks "CELESTRA" and "HOLMESTRA".

The nonwoven fabric web 24' is preferably treated with an effective amount of surface active agent or surfactant. The surfactant provides the nonwoven fabric's surface with greater polarizability than it would have without the surfactant being added. Higher surface polarity yields higher wettability. Suitable surfactants include a product known commercially as ATMER 645 manufactured by ICI Specialty Chemicals.

The nonwoven fabric 24 may be treated with a surfactant prior to or during the time it is manufactured. For example, it may be treated after it is unwound from supply roll 102, or at any other time during the process described herein. The surfactant may be applied to either surface of the nonwoven fabric. This may be done by any known techniques, such as by spraying, by padding, or by the use of transfer rolls. The surfactant can alternatively (or additionally) be incorporated into the nonwoven fabric such as between or within the fibers of the nonwoven fabric. Preferably, the nonwoven fabric is treated with a surfactant prior to the time it is supplied in the present process.

The thermoplastic material is fed into the process at the place indicated B. The second supply source 104 feeds a second material 26' used to make the thermoplastic film 26 into the system. The second material 26' can be any of those materials specified above as being suitable for use in making the thermoplastic film 26. The thermoplastic material is supplied by any suitable supply source 104. Thus, the second supply source could be any conventional means used to introduce a film into a process. The second supply source 104 could be, but is not limited to an unwind roll, a film producing machine, or a supply of resin pellets from which the film is to be made. In the embodiment of the process illustrated, the second supply source is a die 104 in which thermoplastic material is extruded and from which the thermoplastic material flows.

The apertured plastic film 26 should also be treated with an effective amount of a surfactant. Treating the film with a surfactant is particularly helpful in eliminating a prior problem of liquids passing through the nonwoven material, and collecting at the interface between the nonwoven material and the apertured film and then passing back through the nonwoven to contact the wearer's skin. The surfactant, thus, enhances the permeability completely through the topsheet 12.

The apertured plastic film 26 may be treated with the surfactant in any of the general manners specified above (that are not inherently limited to use with fibrous materials). Preferably, a small amount of surfactant is compounded into the resin pellets from which the film 26 is made. The surfactant can be compounded into polyolefin resin pellets such as polyethylene resin pellets. After processing, the surfactant chemical additive exudes to the film surface. Such exudation is due to the insolubility of the additive in the polyolefin at normal temperatures. During extrusion, the molten amorphous resin mass is quenched to a semi-crystalline web. As the ordered crystalline structure forms, the amorphous volume decreases. Since the additive molecules are incompatible in the crystalline structure and insoluble in the cooling amorphous region, they are squeezed or caused to migrate to the surface of the polyolefin.

The surfactant can be the same product referred to above known commercially as ATMER 645. The amount of the surfactant added should be an amount sufficient to render the desired fluid transport through the topsheet 12 (after the corona discharge treatment described below). When a surfactant treated nonwoven fabric, is used, the amount of surfactant is preferably from about 0.5 to about 1%, by weight, of the surfactant in relation to the thermoplastic material. If a non-treated nonwoven fabric is used, from about 2 to about 5% surfactant, by weight, in relation to the thermoplastic material should be used. It is believed that the excess surfactant may migrate into the nonwoven fabric.

The die 104 supplies the thermoplastic material as a hot film 26' which moves along a predetermined path. In the present embodiment, a rotary cylindrical vacuum drum 126 is located along the predetermined path. The nonwoven fabric web 24' is moved past an application roller 128 so that it comes in contact with the hot film 26'. The nonwoven fabric web 24' travels with the hot film 26' along the side of the drum 126. The film 26' is applied to the drum 126 where the nonwoven fabric web 24' is bonded to the hot film 26' by vacuum lamination to form a composite web 12'.

The three-dimensional apertures are formed by placing a perforated three-dimensional forming element or screen on the drum 126. As the film 26' is moved along the drum, an air pressure differential is applied across the film 26' toward a portion of the screen sufficient to distort the film into the perforations of the forming element. The pressure differential thus created causes a forming and rupture of the film 26'resulting in three-dimensional apertures. A process that can be used to create three-dimensional apertures in plastic film is described in detail in U.S. Pat. Nos. 4,351,784, 4,456,570 and 4,535,020.

The composite web 12' passes between nip rollers 134 and 136 past a roller 138 to a corona treating roller 140. Although the chemically treated composite web 12' is more polar than an untreated web, corona discharge treatment of the web 12' provides the desired maximum wettability. The corona treating roller 140 is usually covered with a suitable dielectric material such as epoxy, fluorinated polyethylene ("TELFON"), chlorinated polyethylene ("HYPA-LON"), or polyester ("MYLAR"). The electrode or corona bar 142 is suspended parallel to the corona treating roller 140 at about 16 mm above the roll. The corona bar 142 is energized by a transformer and corona treating power source 144. The above described corona discharge treatment is described in detail in U.S. Pat. Nos. 4,351,784, 4,456,570 and 4,535,020. This completes the formation of the topsheet material 12.

The finished topsheet material 12 continues past a second tension roller 146 to a slitter 148 where it is slit. The topsheet material 12 then proceeds past rollers 150 and 152 to winder 154.

In alternative embodiments of the process of making the topsheet 12, the nonwoven material 24 and the film 26 can be secured in other manners. Typically, in these other processes the nonwoven material 24' is not applied to the film until after the film is cooled. In one alternative process, adhesives can be used to bond the nonwoven material 24 and the film 26 at their faces. In an adhesive bonding process, adhesive can be applied by any suitable commercial adhesive supply device. The adhesives can be applied using any suitable process. For example, the components may be separately manufactured and pre-coated with a pressure-sensitive adhesive, and thereafter secured in a subsequent process. In another example, adhesive could be applied to the nonwoven fabric 24 and the film 26 in a process similar to that shown in FIG. 9, and these two components could be pressed together and bonded when they pass through the nip between nip rollers 134 and 136. Such adhesive bonding processes could, alternatively, be conducted without the application of pressure. In other embodiments, one of the rollers 134 or 136 could be provided with a pattern and the other could serve as an anvil roller, and the two components could be bonded together in the presence of heat and/or pressure. In still other embodiments, the rollers 134 or 136 could be replaced by a commercially available ultrasonic welding device.

It is believed that the absorbent article 10 exhibits good strikethrough times and rewet values. Strikethrough time is a measure of the time liquid takes to penetrate through the topsheet 12. Rapid penetration of the topsheet 12 (i.e., low strikethrough time) is important to reduce the possibility of liquid running over the surface of topsheet 12. Strikethrough may be determined using any suitable procedure. The shorter the strikethrough time, the better the strikethrough characteristics of the topsheet 12. The rewet value is a measure of the amount of liquid which flows from the absorbent core 16 to the outer surface of the topsheet 12. Large quantities of liquid on the outer surface of the topsheet 12 (i.e. high rewet values) are undesirable because they lead to the discomfort of the wearer of the disposable absorbent article. The rewet value of an absorbent article may be determined using any suitable procedure. Suitable procedures for measuring strikethrough and rewet are described in U.S. Pat. No. 4,324,247 issued to Aziz. In an alternative version of the tests described in the Aziz patent, however, the rewet value is determined by subjecting the test sample to a pressure of about 1 psi.

The nonwoven fabric and surfactant-treated apertured film topsheet provides an article that has aesthetic qualities superior to that of the plastic film alone and functional properties superior to that of the nonwoven fabric alone. The nonwoven fabric provides a skin contact layer that is soft and aesthetically pleasing. When the film layer is three-dimensional and apertured, the film layer provides transport of fluids through the film and to an absorbent core while providing a barrier to fluid escape from the core that is difficult with a nonwoven fabric alone.

It will be understood by those skilled in the art that the invention has been described with reference to an exemplary preferred embodiment and that variations and modifications can be effected in the described embodiment without departing from the scope and spirit of the invention.

What is claimed is:

1. A liquid pervious topsheet for an absorbent article, said topsheet comprising a fibrous nonwoven material and an apertured plastic film placed together so that at least a portion of the fibers of said nonwoven material are embedded in some portion of said film, wherein said film is treated with a surfactant to enhance the overall permeability of said topsheet.

2. The topsheet of claim 1 wherein said film is comprised of a thermoplastic resinous material and said surfactant was mixed with said thermoplastic resinous material and incorporated into said film.

3. The topsheet of claim 1 wherein said nonwoven material is also treated with a surfactant.

4. An absorbent article having a body-facing side, said absorbent article comprising:

a liquid pervious topsheet, said topsheet comprising a fibrous nonwoven material that forms the body-facing side of said absorbent article, and an apertured plastic film that underlies said nonwoven material, wherein at least a portion of the fibers of said nonwoven material are embedded in some portion of said film and said film is treated with a surfactant to enhance the overall permeability of said topsheet;

a liquid impervious backsheet joined to said topsheet; and an absorbent core positioned between said topsheet and said backsheet.

5. The absorbent article of claim 4 wherein said film is comprised of a thermoplastic resinous material and said surfactant was mixed with said thermoplastic resinous material and incorporated into said film.

6. A liquid pervious topsheet for an absorbent article having a body-facing side, said topsheet comprising a fibrous nonwoven material and an apertured, thermoplastic film placed together in a face-to-face relationship so that said nonwoven material forms the body-facing side of the absorbent article, and said film underlies said nonwoven material such that at least a portion of the fibers of said nonwoven material are embedded in some portion of said film, wherein said film is comprised of a liquid impervious thermoplastic resinous material which is treated with a surfactant to enhance the overall permeability of said topsheet, and said film has a thickness of from about 0.001 to 0.002 inches and is provided with tapered capillaries in the form of frustums of cones that define apertures, said tapered capillaries each having a base opening adjacent said nonwoven material and an oppositely disposed apex opening, an angle of taper of from about 10° to about 60°, a base opening dimension of from about 0.006 to about 0.250 inch, and an apex opening dimension of from about 0.004 to about 0.100 inch.

7. A composite liquid pervious topsheet for an absorbent article having a body-facing side, said topsheet comprising:

a nonwoven material comprising a plurality of fibers, said nonwoven material having a body-facing side and a garment-facing side, said fibers comprising thermally bonded polypropylene fibers, said nonwoven material having a basis weight from about 8 g/sq. m to about 12 g/sq. m;

and a three-dimensional plastic film having a body-facing side and a garment-facing side and comprised of a liquid impervious thermoplastic resinous material, said film being provided with a plurality of apertures and having a surfactant therein to enhance the overall permeability of said topsheet; wherein:

said nonwoven material and said film are arranged so that said body-facing side of said nonwoven material is disposed above said body-facing side of said film, and said garment-facing side of said nonwoven material lies between said body-facing side of said film and said garment-facing side of said film.

* * * * *